(12) United States Patent
Wu et al.

(10) Patent No.: US 10,124,176 B2
(45) Date of Patent: Nov. 13, 2018

(54) SYSTEM AND METHOD FOR OPERATING AN IMPLANTABLE MEDICAL DEVICE THROUGH RADIO FREQUENCY SIGNALS

(71) Applicant: Pacesetter, Inc., Sunnyvale, CA (US)

(72) Inventors: Yongjian Wu, Saratoga, CA (US); Eric Husky, Mountain View, CA (US); David Doudna, Sunnyvale, CA (US); Chao-wen Young, Cupertino, CA (US); Min Yang, Los Altos, CA (US); Robert Romano, Uppsala (SE); Tommy Akkila, Jafallo (SE); Goran Budgifvars, Spanga (SE); Eduardo Serrano, Valencia, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 12 days.

(21) Appl. No.: 13/974,464

(22) Filed: Aug. 23, 2013

(65) Prior Publication Data
US 2015/0057717 A1 Feb. 26, 2015

(51) Int. Cl.
*A61N 1/372* (2006.01)

(52) U.S. Cl.
CPC ..... *A61N 1/37252* (2013.01); *A61N 1/37235* (2013.01); *A61N 1/37264* (2013.01)

(58) Field of Classification Search
CPC ............ A61N 1/37235; A61N 1/37252; A61N 1/37264
USPC ......................................... 607/30, 32, 59, 60
See application file for complete search history.

(56) References Cited

U.S. PATENT DOCUMENTS

| | | | |
|---|---|---|---|
| 8,088,075 B2 | 1/2012 | Ljunstrom et al. | |
| 2005/0021095 A1* | 1/2005 | Rueter et al. | 607/9 |
| 2005/0049656 A1* | 3/2005 | Petersen et al. | 607/60 |
| 2007/0239229 A1* | 10/2007 | Masoud et al. | 607/60 |
| 2011/0160786 A1 | 6/2011 | Stubbs et al. | |
| 2012/0109260 A1 | 5/2012 | Stancer et al. | |

OTHER PUBLICATIONS

Pham, Dac C. "Overview of the Architecture, Circuit Design, and Physical Implementation of a First-Generation Cell Processor." IEEE Journal of solid-state circuits. vol. 41, No. 1. Jan. 2006.*
Sasaki, Galen H. "Single Cycle Processor". Nov. 26, 2003. EE 361, University of Hawaii. Course Notes. Web. Jun. 27, 2018 <http://ee.hawaii.edu/~sasaki/EE361/Fall03/EE361-SingleMIPS.pdf>.*

* cited by examiner

*Primary Examiner* — Allen Porter, Jr.
(74) *Attorney, Agent, or Firm* — Theresa A. Raymer

(57) ABSTRACT

An implantable medical device (IMD) may include a communication module, a therapy control module, a firmware control module, and a service application. The communication module is configured to wirelessly communicate over an RF link with an external device. The therapy control module is configured to deliver therapy to the patient, and may include a reprogrammable therapy logic circuit configured to operate the therapy control module in a reprogrammable mode of operation, and base-therapy state machine (BTSM) logic circuit configured to operate the therapy control module in a base therapy mode of operation. The firmware control module may include CPU and a memory. The service application may be stored in the memory. The firmware control module is configured to launch the service application, and the BTSM logic circuit provides a base level of sensing and pacing therapy while the communications module in parallel maintains the RF link with the external device.

24 Claims, 10 Drawing Sheets

SYSTEM AND METHOD FOR OPERATING AN IMPLANTABLE MEDICAL DEVICE THROUGH RADIO FREQUENCY SIGNALS

BACKGROUND OF THE DISCLOSURE

Embodiments of the present disclosure generally relate to implantable cardiac devices, and more particularly to implantable medical devices that communicate with an external device through radio frequency (RF) signals.

Numerous medical devices exist today, including but not limited to electrocardiographs ("ECGs"), electroencephalographs ("EEGs"), squid magnetometers, implantable pacemakers, implantable cardioverter-defibrillators ("ICDs"), neurostimulators, electrophysiology ("EP") mapping and radio frequency ("RF") ablation systems, and the like. Implantable medical devices (hereafter generally "implantable medical devices" or "IMDs") are configured to be implanted within patient anatomy and commonly employ one or more leads with electrodes that either receive or deliver voltage, current or other electromagnetic pulses (generally "energy") from or to an organ or tissue (collectively hereafter "tissue") for diagnostic or therapeutic purposes.

Various IMDs are programmed and monitored by an external programmer or external home-based patient care system. For example, a patient may have an IMD that communicates with a base station within the patient's home or a programmer that is used by physicians to change settings within the IMD and/or retrieve data from the IMD. The base station or external programmer device receives data from the IMD about the patient's physiological state. For example, the IMD may transmit stored data or sensed physiological parameters to the base station. Based on the received data, the base station or external programmer device may adjust operating parameters for the IMD.

Conventional external programmers and base stations employ inductive communication techniques that facilitate communication between the IMD and a telemetry wand that is operatively connected to the base station. Typically, the wand of the base station or programmer is placed in close proximity to the IMD in order to establish a communication link. More recently, however, IMD telemetry assemblies have been proposed that employ far-field RF data communication techniques that do not require close proximity between the IMD and the wand of the programmer or base station. Further, some systems do not even include a separate and distinct telemetry wand, and the RF circuitry and antenna are embedded within the housing of the external programmer device or home base station.

Many telemetry systems communicate with IMDs using the Medical Implant Communication Service (MICS) band. Generally, the MICS band is an allocated frequency between 402-405 MHz. The MICS band enables a short-range, wireless link to be maintained between low-power implanted IMDs and an external programmer or base station.

In typical inductive telemetry systems that employ a wand, the IMD itself generally does not include a separate and distinct microprocessor that handles communication with the external device. Instead, in order to establish communication with the device, the wand is positioned in close proximity to the IMD, such as over a chest of an individual.

In contrast, typical RF-based IMDs include a microprocessor that is configured to handle communication with an external device, as well as control patient therapy. A typical RF-based IMD does not include hardware that handles a communication protocol. Instead, the microprocessor runs and operates to conduct RF communication with the external device. As an example, the microprocessor may run communication firmware in order to communicate with the external device.

IMDs may also operate based on tiered therapy. Each IMD may include a standard therapy mode in which the IMD operates to provide therapy to the patient. However, each IMD may also include a backup or restricted mode. The backup or restricted mode is activated if a malfunction or failure is detected within the IMD. The backup or restricted mode ensures that the IMD still provides basic therapy to the individual until the malfunction or failure is corrected, such as through a firmware update or patch that is communicated to the IMD through inductive telemetry, for example. That is, in order to update firmware or software on an IMD, even an RF-based IMD, a telemetry wand is typically used to communicate with the IMD and upload the firmware or software to the IMD.

In an RF-based system, during the backup or restricted mode, the microprocessor that typically is used to communicate with the external device is deactivated and reset. In short, the microprocessor may not run at all during the backup or restricted mode. Accordingly, RF communication with the external device is typically not possible, and there is no communication between the IMD and the external device. As noted above, in order to communicate with the external device, inductive telemetry, such as through use of a wand, is initiated.

Therefore, typical RF-based IMDs generally include inductive telemetry communication interfaces, such as telemetry coils, in order to communicate with the external device during a backup or restricted mode. Further, typical RF-based IMDs are able to download firmware and software upgrades through separate and distinct telemetry communication interfaces. As such, the cost and time of manufacturing a typical RF-based IMD is increased because of the separate and distinct inductive telemetry communication interfaces.

SUMMARY

Certain embodiments of the present disclosure provide an implantable medical device (IMD) configured to be implanted within a patient and communicate with an external device remote from the patient. The IMD may include a communication module, a therapy control module, a firmware control module, and a service application. The communication module is configured to wirelessly communicate over an RF link with the external device. The therapy control module is configured to deliver therapy to the patient, and may include reprogrammable therapy logic circuit configured to operate the therapy control module in a reprogrammable mode of operation, and a base-therapy state machine (BTSM) logic circuit configured to operate the therapy control module in a base therapy mode of operation. The firmware control module may include a central processing unit (CPU) and a memory. The service application may be stored in the memory. The firmware control module is configured to launch the service application. The BTSM logic circuit provides a base level of sensing and pacing therapy while the communications module in parallel maintains the RF link with the external device. Notably, even in the event of a catastrophic system malfunction in which even the service application is unable to run, the BTSM logic circuit still provides a base level of sensing and pacing therapy.

The firmware control module launches the service application upon detection of one or both of a device irregularity or a communication signal from the external device. The service application may be configured to remedy the device irregularity or update the IMD. The device irregularity may include one or more of attempts by the CPU to write to a restricted portion of the memory, corruption of a portion of the memory, the therapy control module administering improper therapy to a patient, or overly-attenuated signal transmission. The communication signal from the external device may include update data configured to update firmware or software of at least a portion of the IMD.

The firmware control module may be configured to initiate an uncontrolled launch of the service application when one or more of the communication module, the therapy control module, or the firmware control module is malfunctioning. The firmware control module receives an error signal when one or more of the communication module, the therapy control module, or the firmware control module are malfunctioning that triggers the uncontrolled launch of the service application.

The service application is configured to support RF-based firmware download and allow the launch of a clinical firmware application. The service application may be configured to deactivate one or more hardware circuits of the IMD. The service application may be configured to record an instantaneous functional operational state of one or more of the communication module, the firmware control module, and therapy control module when the service application is activated.

The firmware control module may also include an interrogator configured to monitor operation of the IMD and detect the one or both of the device irregularity or the communication signal from the external device. The firmware control module may also include a scratchpad memory. The CPU is configured to access the scratchpad memory during the base therapy mode.

The IMD may also include a patient connection interface operatively connected to the therapy control module. The patient connection interface may be configured to connect the therapy control module to at least one anatomical structure of the patient. The patient connection interface may include one or more leads.

The firmware control module may also include a random access memory (RAM). The CPU may be prevented from accessing the RAM during the base therapy mode. For example, the IMD may be unable to automatically exit BTSM logic without external intervention because, if the IMD transitions to BTSM logic, the IMD may generally be experiencing an error. As such, the BTSM logic may be active and an external programmer may intervene to either fix the error and subsequently transition out of BTSM logic, or indicate that the IMD should be replaced as soon as possible.

The communication module may include one or more of an RF transceiver and an RF antenna. The communication module is configured to communicate with the external device through RF signals. The communication module may be devoid of a telemetry coil configured to communicate through inductive communication.

The memory of the firmware control module may include read-only memory (ROM), which may include a subset of the memory that includes the service application.

Certain embodiments of the present disclosure provide a method of operating an implantable medical device (IMD) that is implanted within a patient. The method may include wirelessly communicating with an external device over an RF link using a communication module of the IMD, and delivering therapy to a patient with a therapy control module. The delivering operation may include operating the therapy control module in a reprogrammable mode of operation using a reprogrammable therapy logic circuit configured to operate the therapy control module in a reprogrammable mode of operation, and operating the therapy control module in a base therapy mode of operation using a base-therapy state machine (BTSM) logic circuit. The method may also include launching a service application with a firmware control module. The launching operation activates the BTSM logic circuit to provide a base level of sensing and pacing therapy while the communications module in parallel maintains the RF link with the external device.

DETAILED DESCRIPTION

Figure 1:
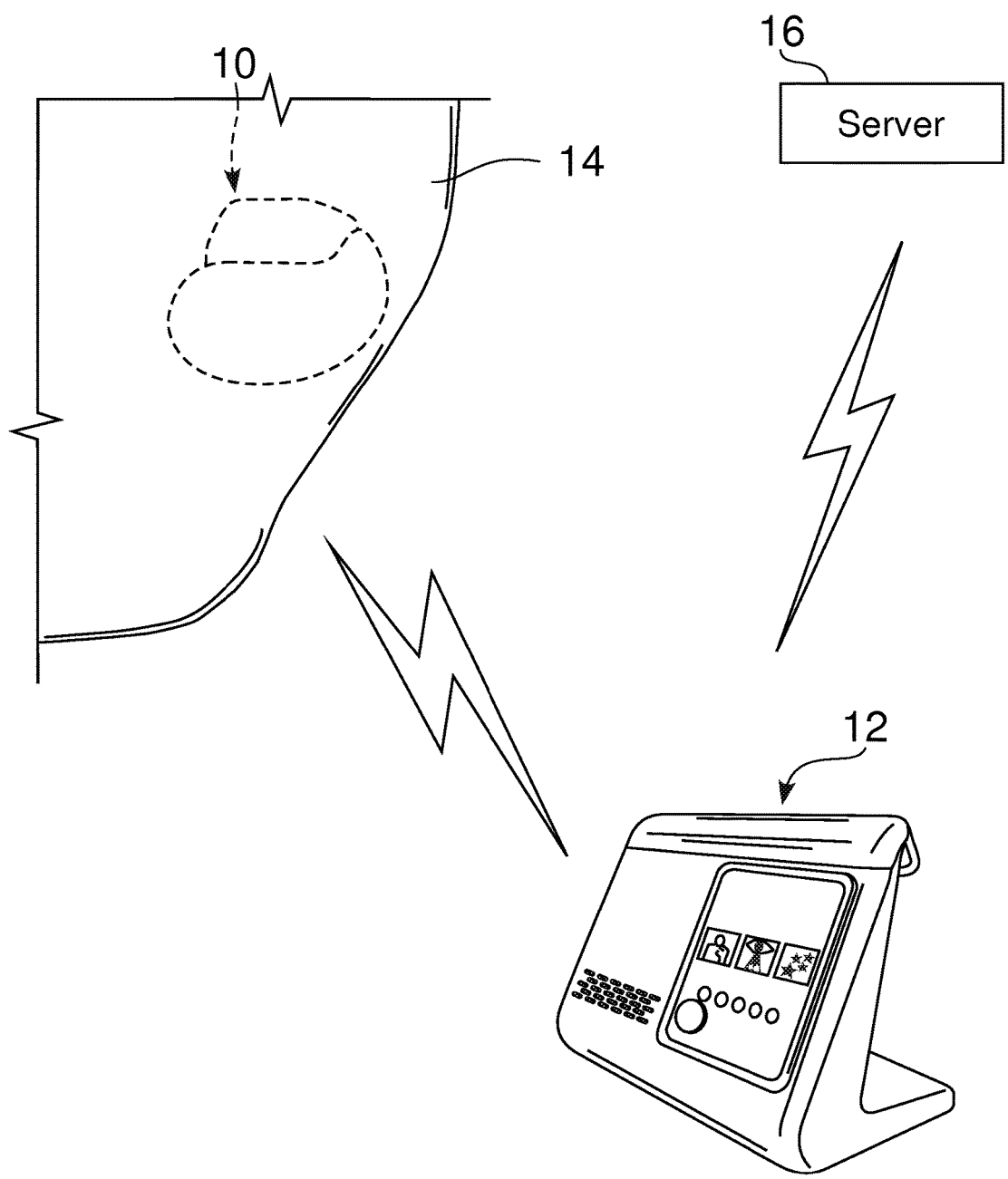
FIG. 1 illustrates a simplified view of an IMD and patient care system (PCS), according to an embodiment of the present disclosure.

FIG. 1 illustrates a simplified view of an IMD 10 and external device, such as a patient care system (PCS) 12, according to an embodiment of the present disclosure. The IMD 10 may be implanted within a patient 14. The remotely-located PCS 12 monitors the IMD 10. The PCS 12 may be located within a home of the patient 14, in his/her vehicle, at his/her office and the like. When, the PCS 12 is located within the patient's home, the PCS 12 may be proximate a bed of the patient 14. The PCS 12 functions as a base station that wirelessly communicates with the IMD 10. The PCS 12 may also communicate with a remote server 16 within a patient care network, such as over a phone link, cellular link, Internet connection, local area network, wide area network and the like.

The PCS 12 performs various functions, such as operating as an intermediate relay device to collect and store patient physiologic data, IMD operational status data and the like. The physiologic data may be electrical data related to a physiologic condition. The PCS 12 may then transmit the physiologic data, IMD operational status data and other data to the remote server 16 of the patient care network. Physicians and other personnel can monitor the patient and collect data over the patient care network. Also, the PCS 12 may receive updates, upgrades and other IMD control-related information from the patient care network and relay the IMD control-related information to the IMD 10.

Alternatively, the PCS 12 may not be used. Instead, data from the IMD 10 may simply be accessed at an office of a physician, for example.

The IMD 10 may be one of various types of implantable devices, such as, for example, an implantable pacemaker, implantable cardioverter-defibrillator ("ICD"), defibrillator, cardiac rhythm management ("CRM") device, neurostimulator, electrophysiology ("EP") mapping and radio frequency ("RF") ablation system, or the like.

The PCS 12 may include a standalone antenna assembly. The PCS 12 may represent the Merlin® home patient care system offered by St. Jude Medical. The PCS 12 may include an RF telemetry subsystem that communicates with the IMD 10 and/or the server 16. The telemetry subsystem may include an RF telemetry circuit operatively connected to one or more MICS antennas. The telemetry circuit may also be operatively connected to a controller or processing unit. Alternatively, the PCS 12 may represent a handheld portable tablet-type programmer device used by physicians and others to communicate with, collect data from, program and reprogram, the IMD 10. Also, alternatively, the PCS 12 may be a cell phone, personal computer, or laptop computer.

Figure 2:
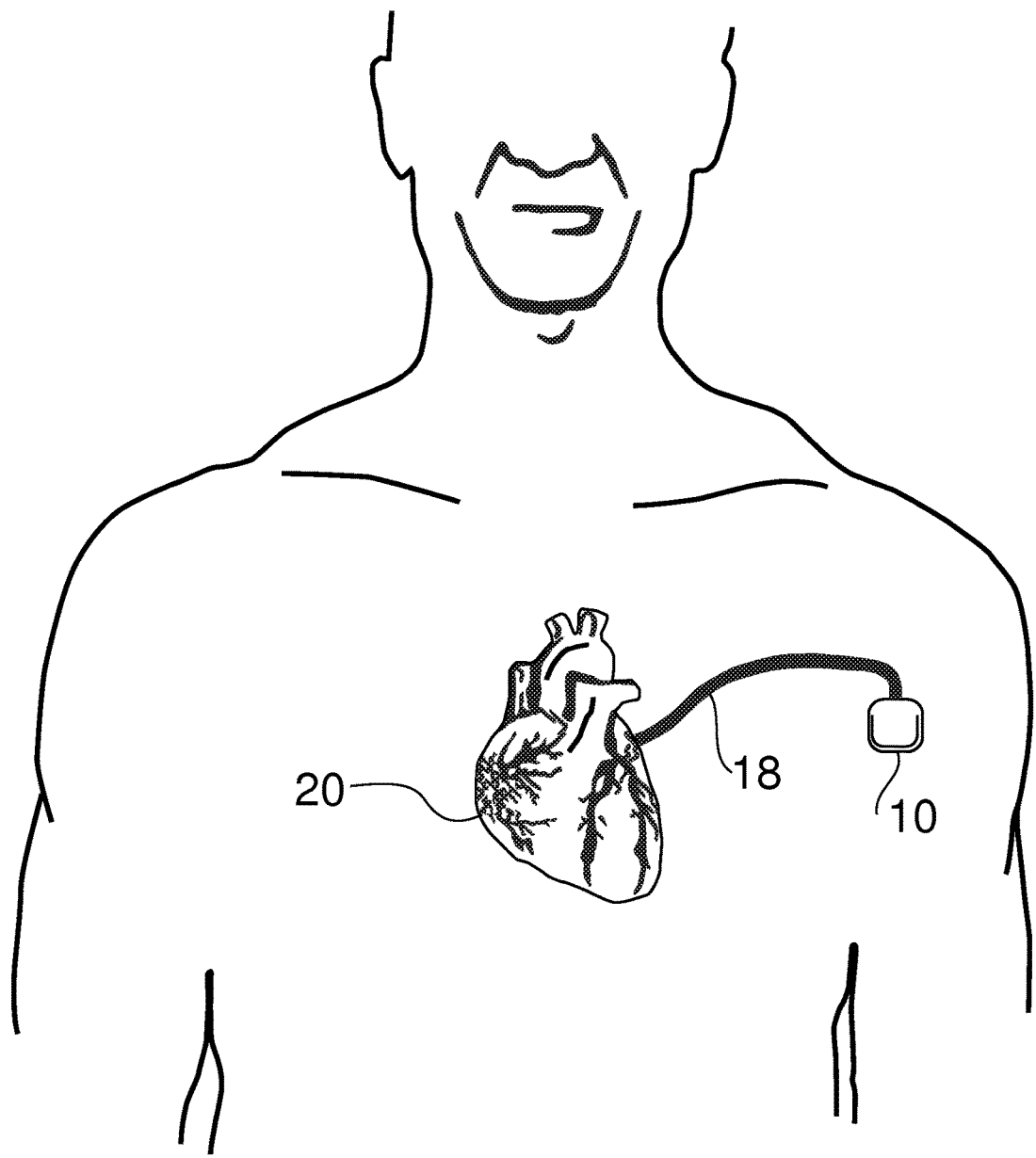
FIG. 2 illustrates an IMD implanted in a patient, according to an embodiment of the present disclosure.

FIG. 2 illustrates the IMD 10 implanted in the patient 14, according to an embodiment of the present disclosure. The IMD 10 may be an implantable pacemaker, for example. One or more leads 18 provide a patient connection interface that connects the IMD 10 to the heart 20, for example. The IMD 10 may provide therapy, such as stimulation of the heart 20 and rhythm control, through the lead(s) 18. In order to transmit and receive RF signals, the IMD 10 may include a transceiver and/or an antenna.

Figure 3:
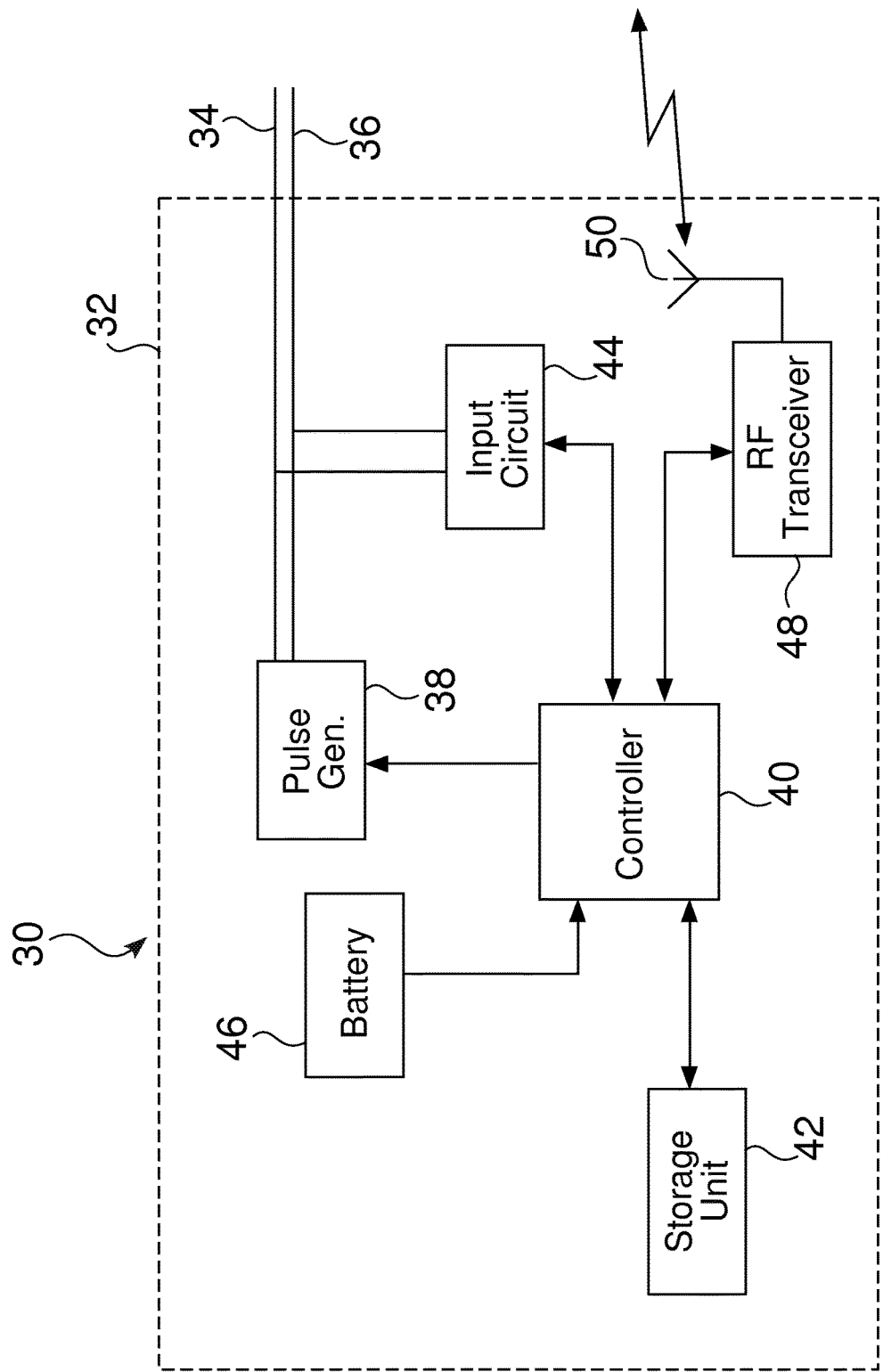
FIG. 3 illustrates a functional block diagram of an IMD, according to an embodiment of the present disclosure.

FIG. 3 illustrates a functional block diagram of an IMD 30, according to an embodiment of the present disclosure. The IMD 30 includes a housing 32 that is hermetically sealed and biologically inert. The housing 32 may be conductive and may thus serve as an electrode. The IMD 30 may be connectable to one or more leads, such as a ventricular lead 34 that is configured to be implanted in a right ventricle of the heart and an atrial lead 36 that is configured to be implanted in a right atrium of the heart. The leads 34 and 36 may include one or more electrodes, such as a tip electrode or a ring electrode that may be configured to measure impedance, measure cardiac signals, and/or transmit pacing pulses for causing depolarization of cardiac tissue adjacent to the electrodes. The pacing pulses are generated by a pace pulse generator 38 in response to directions provided from a controller or controlling circuit 40 that may include a microprocessor. The controller 40 is configured to control parameters, such as pace pulse parameters. The pace pulse parameters may include output voltage and pulse duration, for example. An example of the electronics within the IMD 30 are described below in more detail in connection with FIG. 10.

A storage unit 42 may be connected to the controller 40. The storage unit 42 may include a random access memory (RAM), a non-volatile memory, such as a read-only memory (ROM), a scratchpad memory, and the like. Detected signals from the patient's heart may be processed by an input circuit 44 and forwarded to the controller 40 for use in logic timing determination. The IMD 30 may be powered by a battery 46, which supplies electrical power to all active electrical components of the pacemaker.

The IMD 30 may include an RF transceiver 48 for wireless communication of signals to/from an external programmer, a patient care assembly, and the like. Medical personnel may prefer to monitor and/or adjust parameters of the IMD 30 or to perform reprogramming. The transceiver 48 may be connected to an antenna 50.

Figure 4:
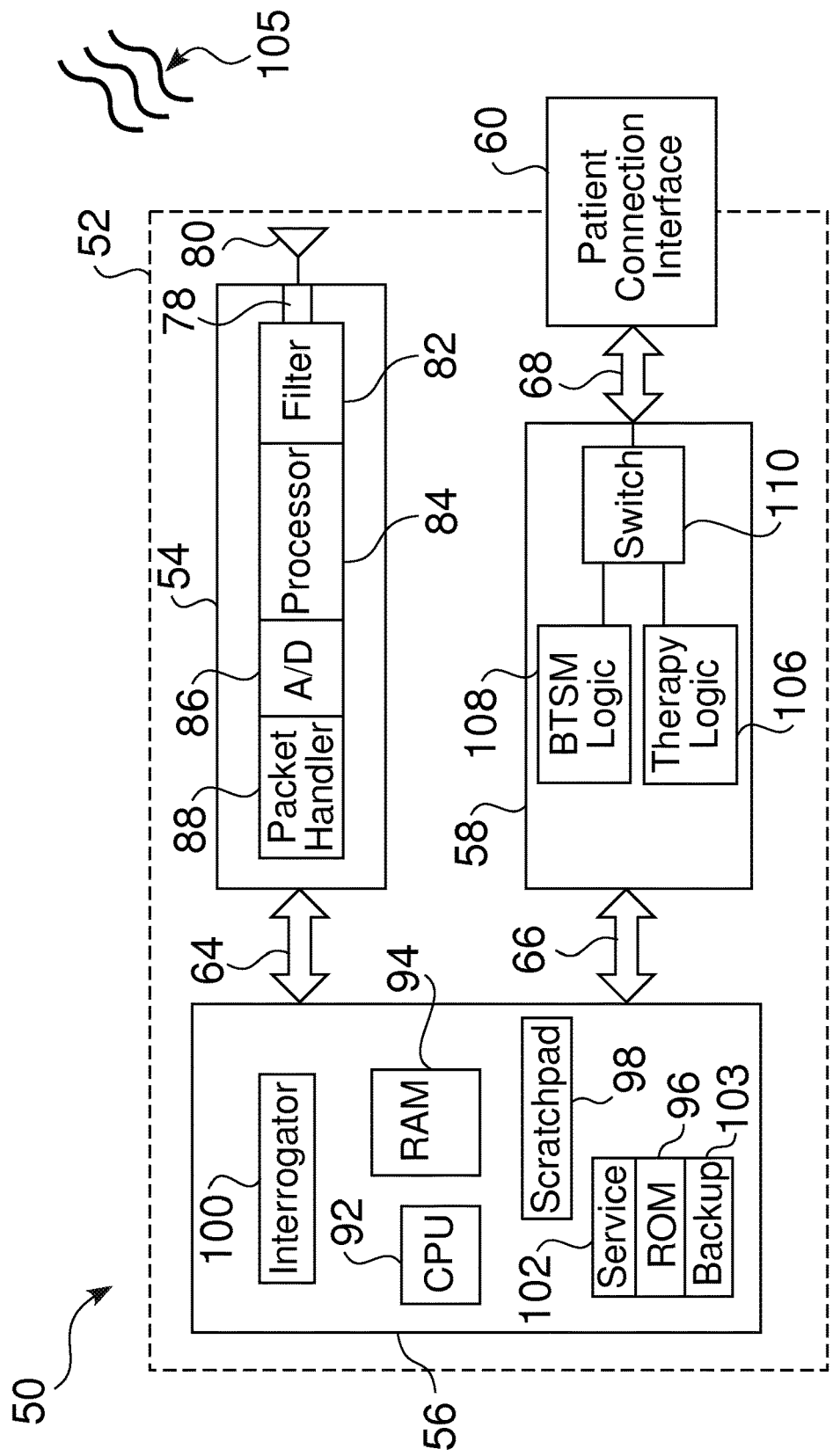
FIG. 4 illustrates a schematic block diagram of select subassemblies within an IMD, according to an embodiment of the present disclosure.

FIG. 4 illustrates a schematic block diagram of select subassemblies within an IMD 50, according to an embodiment of the present disclosure. The IMD 50 includes a housing 52 that contains a communication module 54 that is operatively connected to and in communication with a firmware control module 56. The firmware control module 56 is operatively connected to and in communication with a therapy control module 58, which is, in turn, operatively connected to a patient connection interface 60, such as lead(s), electrodes, and/or the like. The IMD 50 may include any of the components described with respect to FIGS. 3 and 10. For example, the controller 40 shown in FIG. 3 may include one or more integrated circuits that include the communication module 54, the firmware control module 56, and the therapy control module 58.

The communication module 54 may include an internal transceiver 78 which is operatively connected to an antenna 80. The communication module 54 is configured to communicate with an external device, such as the PCS 12 shown in FIG. 1, by way of the transceiver 78 and the antenna 80. The communication module 72 may include an MCIS radio controller chip, for example. The transceiver 78 and the antenna 80 may be configured to allow for bi-directional, wireless RF communication with the external device. The antenna 80 and/or the transceiver 78 may be built into the IMD 70 and connected to the communication module 72 through a flex cable, for example. The communication module 54 may also include a data filter 82 operatively connected to a processor 84. The communication module 72 may also include an analog-to-digital (A/D) converter 86 and a packet handler 88.

The communication module 54 may be operatively connected to the firmware control module 56 through a bi-directional communication interface 64, such as a serial communication interface. In operation, a data signal is received from an external device through the antenna 80. The data is sent to the data filter 82, which filters the analog RF signal received over the air through one or more RF signals. After the filtering, the processor 84 processes the data signal and the A/D converter 86 converts the data signal from analog to digital, at which point the digitized data signal is sent to the packet handler 88, which prepares the digital, packetized data signal for transmission to the firmware control module 56 over the bi-directional interface 64.

The firmware control module 56 may include a digital core and dedicated serial interface that communicates and controls the communication module 54. The firmware control module 56 is configured to run firmware and manage therapeutic functions of the INC 50. The firmware control module 56 may include a control unit, such as a central processing unit (CPU) 92, which may be or include a microcontroller, microprocessor, integrated circuit, and/or the like. The CPU 92 is in communication with random access memory (RAM) 94, read-only memory (ROM) 96, a scratch pad memory 98, and an interrogator 100. The ROM 96 may include a subset reserved for a service application 102 and a backup therapy application 103. The service application 102 and the backup therapy application 103 may be subsets of the ROM 96. Optionally, the backup therapy application 103 may be contained within the service application 102. The firmware control module 56 is connected to the therapy control module 58 through a bi-directional interface 66, such as a register access interface or serial communication interface, for example.

The therapy control module 58 may include therapy logic circuit 106 and base-therapy state machine (BTSM) logic circuit 108 connected to a switch 110. The BTSM logic circuit includes BTSM logic. A state machine is generally a logical construct that transitions among a finite number of states. A state machine is generally in one state at a particular point in time. The state machine moves between states depending upon a number of triggers. For example, the BTSM state machine logic circuit is configured to move between a regular or normal mode of operation and a safe mode of operation, as described below. The BTSM logic circuit 108 is configured to operate the therapy control module 58 in a base therapy mode of operation 108. The therapy control module 58 is also connected to a patient connection interface 60. The therapy control module 58 may be operatively connected to the patient connection interface 60 through a bi-directional communication interface 68, such as a serial communication interface, for example.

Each module 54, 56, and 58 may include one or more control units, such as processing devices that may include one or more microprocessors, microcontrollers, integrated circuits, memory, such as read-only and/or random access memory, and the like. The modules 54, 56, and 58 may be integrated into a single module and contained within a single device, such as a single integrated chip, for example. Alternatively, each module 54, 56, and 58, may be its own separate and distinct module, and contained within a respective integrated chip, for example.

One or more of the modules 54, 56, and 58 may include any suitable computer-readable media used for data storage. For example, one or more of the modules 54, 56, and 58 may include computer-readable media. The computer-readable media are configured to store information that may be interpreted by the modules 54, 56, and 58. The information may be data or may take the form of computer-executable instructions, such as software applications, that cause a microprocessor or other such control unit within the modules 54, 56, and 58 to perform certain functions and/or computer-implemented methods. The computer-readable media may include computer storage media and communication media. The computer storage media may include volatile and non-volatile media, removable and non-removable media implemented in any method or technology for storage of information such as computer-readable instructions, data structures, program modules or other data. The computer storage media may include, but are not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which may be used to store desired information and that may be accessed by components of the system.

In operation, the communication module 54 is configured to communicate with an external device, such as the PCS 12 (shown in FIG. 1). The firmware control module 56 may include an interrogator 100, which may include a processing or control unit that is operatively connected to memory. Through the interrogator 100, the firmware control module 56 may monitor the IMD 50 to determine whether or not the IMD 50 is properly functioning. The firmware control module 56 may also detect signals transmitted from the external device that indicate that a software or firmware update is ready for download. The firmware may include a combination of persistent memory, program code, and data stored therein. When the firmware control module 56 detects a system failure or malfunction in the IMD 50, and/or when the firmware control module 56 receives a signal from the external device indicating that an update is ready for download, the firmware control module 56 may transition the IMD 50 from a standard therapy mode to a base therapy mode, such as a service mode (in which the IMD 50 is serviced, repaired, fixed, or the like), backup mode (in which the IMD 50 is updated or the like, and memory is backed up, for example), or restricted mode (in which operation of certain components of the IMO 50 are restricted).

For example, if the interrogator 100 detects a device failure, malfunction, error, or other such device irregularity, the interrogator 100 may send a signal to the CPU 92 indicating such device irregularity. As an example, the interrogator 100, which may be configured to monitor the therapy control module 58, the patient connection interface 60, the communication module 54, and the firmware control module 56, may detect various device irregularities, such as attempts by the CPU 92 to write to the ROM 96, corruption of the RAM 94, the A/D converter 86 being unable to convert analog data to digital data, the therapy control module 58 administering improper therapy to a patient, overly-attenuated signal transmission in the patient connection interface 60, and/or the like. Once the device irregularity is detected, the interrogator 100 sends an irregularity signal indicating the specific device irregularity to the CPU 92. When the CPU 92 receives the irregularity signal, the CPU 92 transitions into a base therapy mode, such as a restricted or bypass mode, in which the CPU 92 may communicate with an external device and/or access the service application 102. During the base therapy mode, the CPU 92 may send a device irregularity signal to the external device through the communication module 54. The external device receives the irregularity signal and matches the irregularity with a remedy specific to the device irregularity. For example, the remedy may be included as remedy data in the form of software or firmware that is sent to and stored in the service application 102. Once the remedy data is downloaded to the service application 102 from the external device, the CPU 92 may access the remedy data within the service application 102, and operate according to the remedy data to remedy the device irregularity. Once the device irregularity has been remedied (for example, the interrogator 100 may detect that the device irregularity no longer exists), the CPU 92 transitions back to the normal mode of operation.

The service application 102 may be stored in a portion of the ROM 96. The service application 102 may include software or firmware configured to recognize device irregularities, which may include device failures, malfunctions, errors, and the like. The device irregularities may include the CPU 92 attempting to write to ROM 96, the energy level of a particular therapy is above or below an acceptable threshold, and/or the like. The CPU 92 accesses the service application 102 to remedy the device failure. Once the device failure is remedied, the firmware control module 56 detects that the IMD 50 is operating normally, and transitions back to a normal mode of operation. Notably, during the base therapy mode, the CPU 92 continues to operate. However, in the base therapy mode, the CPU 92 may operate at a restricted level, that is, not at the same power level and functionality as during the normal mode of operation. Alternatively, during the base therapy mode, the CPU 92 may operate at the same power level as during the normal mode of operation.

The interrogator 100 may monitor and interrogate the various components of the IMD 50 to determine the extent of any device irregularity. As one example, during the restricted mode, the interrogator 100 may monitor whether the IMD 50 is in communication with the external device. If so, the CPU 92 may operate in the normal mode of operation in which the CPU 92 has full read-write access to the RAM 94. If, however, the interrogator 100 determines that communication with the external device is interrupted, then the interrogator 100 may send a device irregularity or status signal to the CPU 92. The CPU 92 may then transition to the base therapy mode and access only the service application 102 and the scratch pad memory 98. The scratch pad memory 98 may be a mechanical register file, for example. The scratch pad memory 98 is generally a smaller, simpler memory than the RAM 94, and may be less subject to potential failure than the RAM 94.

The interrogator 100 may include watchdog logic configured to periodically strobe the communication module 54 to listen for an external instrument wakeup request so that the IMD 50 is RF responsive. Additionally, the watchdog logic may be configured to acknowledge and process any pending RF interrupt from an external device in a timely manner.

In the base therapy mode, the firmware control module 56 directs the therapy control module 58 to enter a backup therapy mode 103, in which basic therapy is still administered to the patient. For example, in the base therapy mode, the therapy control module 58 provides life-critical functions and maintains an expected therapy, such as pacing, defibrillation, sensing, and/or the like to the patient to maintain the health of the patient. However, during the base therapy mode, the CPU 92 within the firmware control module 56 may operate at a reduced state. For example, instead of ceasing all operation, the CPU 92 may function to access a segment of memory, such as within the ROM 96, to service the IMD 10. As described above, for example, the CPU 92 may function to access the service application 102.

During the base therapy mode, the therapy control module 58 switches operation, via the switch 110, from the normal therapy logic circuit 106 to the BTSM logic circuit 108, according to the backup therapy application 103. The BTSM logic circuit 108 provides basic therapy to the patient as the device irregularity is remedied. After the device irregularity is remedied, the therapy control module 54 switches back to the therapy logic circuit 106, for example.

The IMD 50 may be transitioned to the base therapy mode in various ways. For example, the external device may transmit a communication signal to the firmware control module 56 indicating that the external device is to intervene, such as through a firmware or software upgrade. As another example, a user may voluntarily initiate a base therapy mode, such as through the external device, in order to initiate a service audit, by way of the interrogator 100, within the IMD 50. Further, the RAM 94 or ROM 96 may be programmed to cause the CPU 92 to enter the base therapy mode on a periodic basis, such as once a day, once a week, once a month, or the like, in order to provide device diagnostic tests.

The IMD 50 may enter a base therapy mode, such as a backup mode, restricted mode, service mode, or the like, through a variety of triggers. For example, the ND 50 may initiate the base therapy mode upon initial device power-up, a controlled re-start for the purpose of firmware upgrade of a normally-functioning device, a re-start from a device irregularity, such as a device error condition, and/or the like. While firmware is downloaded to the service application 102 within the ROM 96, the therapy control module 106 performs basic therapeutic functions according to the backup therapy application 103. For example, during the base therapy mode, the CPU 92 may operate the switch 110 to deactivate the therapy logic circuit 106 and switch to the BTSM logic circuit 108, which is configured to provide basis, life-critical therapy to the patient.

The firmware control module 56, by way of the CPU 92 accessing the service application 102 and/or the backup therapy application 103 and operating according thereto in the base therapy mode, runs the therapy control module 58 (such as by switching the BTSM logic circuit 108). As such, the BTSM logic circuit 108 provides basic therapeutic functions to the patient during the base therapy mode. The service application 102 may include digital logic and be allocated a portion of the ROM 96, as indicated above. During the base therapy mode, the service application 102 may include instructions and/or hardware that prevent the CPU 92 from accessing the RAM 94, unless there is an active communication with an external device.

As noted above, once a device irregularity is detected, the CPU 92 switches to the backup or restricted mode and contacts the external device for a remedy. Alternatively, the service application 102 may include a plurality of remedy data that the CPU 92 may access before contacting the external device. In this manner, the CPU 92, in the base therapy mode, may determine the proper device remedy and fix the device irregularity without contacting the external device.

Additionally, software or firmware updates 105 may be transmitted to the firmware control module 56 by the external device through the communication module 54. The software or firmware updates 105 may relate to a desired therapy, for example. As one example, a physician may determine that a pacing or defibrillating therapy, for example, may be altered to take into account changing physiological conditions of the patient. As such, the physician may decide to transmit an update 105 to the IMD 50 through the external device. The update 105 is received by the communication module 54 and delivered to the firmware control module 56. The firmware control module 56 may then transition the IMD 50 into the base therapy mode, while the update 105 is stored in the service segment of the memory (for example, the downloaded update 105 may be stored in the ROM 96). The firmware control module 56 may then access the update 105 and update the IMD 50 based on the update 105. Again, the update 105 may relate to any portion of the IMD 50 that is to be updated. As the IMD 50 updates, the firmware control module 56 ensures that the IMD 50 remains in the base therapy mode. Once the update is finished, the firmware control module 50 transitions the IMO 50 back to the normal mode of operation. Thus, the IMD 50 may be updated without the need for a separate and distinct inductive telemetry system.

The firmware control module 56 may download software and firmware updates 105 directly from the external device by way of the communication module 54. The interrogator 100 may continually listen for update signals from the external device. When the interrogator 100 detects the update 105 from the external device, the interrogator 100 may send an update signal to the CPU 92. When the CPU 92 detects the update 105, the CPU 92 may transition the IMD 50 from the normal mode of operation to the base therapy mode, and accept the update 105 from the external device via the communication module 54. The CPU 92 may store the update 105 in the RAM 94 and access the update 105 therefrom in order to update the IMD 50. For example, the therapy logic circuit 106 may be updated. As the IMD 50 is updated, the CPU 92 may remain in the base therapy mode. After the update is completed (as detected by the interrogator 100, for example), the CPU 92 transitions back to the normal mode of operation. Alternatively, the IMO 50 may be updated during a normal mode of operation.

As described above, in the base therapy mode, the CPU 92 may fetch instructions from the service application 92 and communicate with the external device through the communication module 72. As noted, the service application 102 may be a subset of the ROM 96. In general, ROM 96 is a safe, stable part of an integrated chip. However, the service application 102 may be a subset of other parts of the firmware control module 74, such as the RAM 94. Further, during the base therapy mode, the CPU 92 may be able to access the scratch pad memory 98, which may be a smaller read-write memory as compared to the RAM 94.

As described above, when the IMD 50 is transitioned to a base therapy mode, instead of the CPU 92 of the firmware control module 56 ceasing operation, the firmware control module 56 may transition into a reduced functionality state in which a subset of memory, such as the service application 102 or segment within the ROM 96, is activated and may communicate with an external device through RF communication. For example, in the base therapy mode, the CPU 92 within the firmware control module 56 may fetch instructions from the service application 102. At the same time, the therapy control module 58 remains operational for patient therapy. As one example, BTSM logic circuit 108 or a hardware state machine within the therapy control module 58 continues to operate to provide therapy to the patient during the base therapy mode.

During the base therapy mode, the CPU 92 within the firmware control module 56 may operate at a minimum power level that allows for basic RF communication with the external device. Optionally, the CPU 92 may operate at a power level that is greater than a minimum power level that allows for basic RF communication. In the base therapy mode, the firmware control module 56 recovers data received from the external device, such as update data, software bug fixes, firmware or software remedy data, and/or the like. Also, during the base therapy mode, the firmware control module 56 may interrogate the IMD 50 to determine potential problems, system malfunctions, failures, and the like.

The firmware control modules described above may support a limited protocol while communicating with external devices. For example, as described above, the limited protocol may include one or more of a service mode (in which the IMD 50 is serviced, repaired, fixed, or the like), backup mode (in which the IMD 50 is updated or the like, and memory is backed up, for example), or restricted mode (in which operation of certain components of the IMD 50 are restricted). The firmware control modules may implement protocols that allow for: a field upgrade of functioning device firmware; restoration and remedy an IMD error, malfunction, or failure; and basic diagnostic information gathering during the base therapy mode. The limited protocols may be simplified protocols that include one or more of the service mode, the restricted mode, the backup mode, and the like. The limited protocols may be used to correct device irregularities, and allow for firmware upgrades, for example. Each limited protocol may be or include a digital message format and rule for exchange between the external device and the firmware control module 56, for example. The limited protocols may include signaling, authentication and error detection and correction capabilities.

Embodiments of the present disclosure provide an IMD that may include a firmware control module and a therapy control module. When the firmware control module detects a device irregularity or update signal, the firmware control module transitions to a base therapy mode while the therapy control module continues to operate life-critical functions of the IMO.

As explained above, the communication module 54 wirelessly communicates over an RF link with the external device, such as the PCS 12 shown in FIG. 1. The therapy control module 58 is configured to deliver therapy to a patient. The therapy control module 58 includes the therapy logic circuit 106, which may be reprogrammed through a device update and/or through operation of the service application 102, the backup therapy logic circuit 103, and/or the like. As such, the therapy logic circuit 106 is configured to operate the therapy control module 58 in a reprogrammable mode of operation. The therapy control module 58 also includes the BTSM logic circuit 108, which is configured to operate the therapy control module 58 in a base therapy mode of operation. The service application 102 is stored in the memory, such as within a portion of the ROM 96. The firmware control module 56 is configured to launch the service application 102, and the BTSM logic circuit 108 provides a base level of sensing and pacing therapy while the communications module 54 in parallel maintains the RF link with the external device. Notably, even in the event of a catastrophic system malfunction in which even the service application 102 is unable to run, the BTSM logic circuit 108 still provides a base level of sensing and pacing therapy.

The therapy logic circuit 106 is reprogrammable in that it, through device upgrades and updates, may rearrange its underlying logic. For example, in response to software and/or firmware upgrades or updates, the underlying logic contained within therapy logic circuit 106 may be reconfigured to accommodate improvements to general circuits developed after the ND 50 has been implanted within a patient. As examples, the therapy logic circuit 106 may be reprogrammed to accommodate increased computing power and ability, quicker response time, troubleshooting, and the like. The therapy logic circuit 106 may be or include a field programmable gate array (FPGA), integrated chip, and/or the like, for example. In general, the therapy logic circuit 106, through device upgrades and updates downloaded to the firmware control module 56, may be adaptively programmed to perform tasks with increased efficiency, and/or different tasks related to physiological monitoring, therapy, and the like.

The reprogrammable nature of the therapy logic circuit 106 differs from a mere state machine, which is generally a logical construct that transitions among a finite number of states, as explained above. In contrast, the therapy logic circuit 106 may be reprogrammed to adapt to changing circumstances, device improvements, and the like.

The therapy logic circuit 106 may be reprogrammed after the IMD 50 has been implanted within a patient through a physician within a clinic through a PCS. For example, a physician may reprogram the therapy logic circuit 106 through the use of the Merlin® home patient care system offered by St. Jude Medical. As such, the therapy logic circuit 106 is reprogrammable in that a user, such as a physician, may reprogram the therapy logic circuit 106 after the IMD 50 is implanted within a patient. In contrast, a state machine, such as the BTSM logic circuit 108 is initially programmed by a manufacturer before the ND 50 is implanted within a patient. The state machine may not, however, be reprogrammed once the IMO 50 has been implanted within a patient. Instead, the logic contained within the BTSM logic circuit 108 may be fixed and constant through the life of the IMD 50.

Additionally, the firmware control module may initiate an uncontrolled launch of the service application upon detection of a malfunction within the IMD. For example, the firmware control module may initiate an uncontrolled launch of the service application when one or more of the communication module, the therapy control module, or the firmware control module is/are malfunctioning. The firmware control module may receive an error signal when one or more of the communication module, the therapy control module, or the firmware control module are malfunctioning that triggers the uncontrolled launch of the service application. The launch is "uncontrolled" in that the firmware control module is unable to override or control the initiate of the service application.

Also, the service application may minimally depend on hardware. That is, the service application may be connected to the smallest amount of hardware that allows the service application to be launched and operate. The service application is configured to support an RF-based firmware download and allow the launch of a clinical firmware application. The clinical firmware application may be an application configured to operate and control the ND during a normal or standard mode of operation, for example. The normal or standard mode of operation may include the mode of operation other than the safe mode of operation.

Further, when the service application 102 is launched, hardware within the IMD may deactivate one or more hardware circuits of the IMD. For example, hardware within the ND may be configured to deactivate the therapy logic circuit 106 when the service application is activated by the firmware control module 56. In short, one or more of the hardware circuits used by the clinical firmware application during the normal or standard mode of operation may be deactivated when the service application 102 is launched.

Moreover, the service application 102 may be configured to record an instantaneous functional operation state of the communication module, the firmware control module 56, or the therapy control module 58 when the service application 102 is activated. The recorded functional operation state may be analyzed by the firmware control module and/or the external device to analyze a device irregularity, such as a device failure, for example. As an example, when the service application 102 is launched, the service application 102 may record the structural and/or functional states of all of the hardware within the IMD 50. The firmware control module 56 may transmit the recorded data to the external device, which may then assess the origin of the device irregularity. The external device may then upload an appropriate device remedy to the firmware control module 56, for example. Optionally, the external device may analyze the recorded data to preemptively prevent such a device irregularity in the future. For example, the external device may transmit a software or firmware update to the firmware control module 56 that prevents such a device irregularity from occurring again.

Notably, RF communication between the external device and the IMD 50 may fail during a device upgrade due to environmental interference, patient movement that blocks radio propagation and other failures like software state machine error, and the like. The processor 84 within the communication module 54 may provide basic error handling and notification to the firmware control module 56. Additionally, one or more of the communication module 54, the firmware control module 56, and the therapy control module 58 may include logic to ensure that communication links are open and reliable. If any of the communication links are deactivated, a communication process may be re-initiated. If, after the communication process is re-initiated, communication is still not occurring, the firmware control module 56 may transition the IMD 50 to the safe mode, as described above.

The IMD may also include security software or firmware to prevent hackers from making unauthorized accesses of patient data or downloading bad firmware. For example, the IMD may be configured to communicate with the external device through encrypted communications.

In general, the IMD 50 is configured to provide basic therapeutic functions (such as in a base therapy mode), while the firmware control module 56 executes in the safe mode, such as through operation of the service application 102. In one or more error handling cases, the service application 102 re-starts and resumes operation, but the patient is safe due to the base therapy mode.

Figure 5:
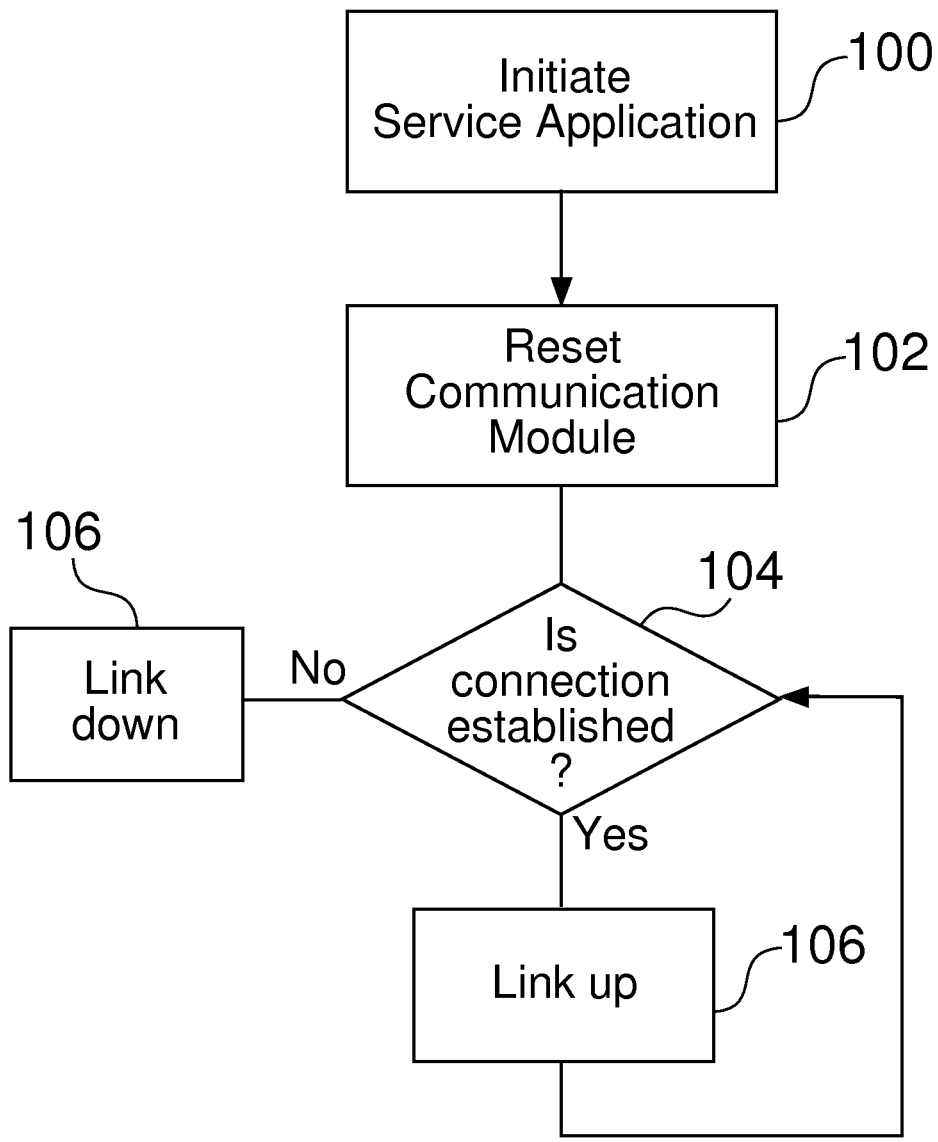
FIG. 5 illustrates a flow diagram of a method for implementing a service application operation, according to an embodiment of the present disclosure.

FIG. 5 illustrates a flow diagram of a method for implementing a service application operation, according to an embodiment of the present disclosure. At 100, the service application is initiated, as described above. For example, in a base therapy mode, the service application may be accessed by a firmware control module 56, such as shown in FIG. 4. At 102, the communication module 54, such as shown in FIG. 4, may be reset and initialized to a low current drain mode, in which it operates at a lower power, but is able to communicate with an external device. At 104, it is determined whether a communication connection is established between the IMO and the external device. If not, the service application may be operated in a link down state at 106, in which the firmware control module 56 draws a minimal amount of battery power. When a connection is established with an external device, the firmware control module 56 enters a link up state at 106. In the link up state, the firmware control module 56 may communicate with the external device. For example, the external device may transmit update or remedy data to the firmware control module.

Figure 6:
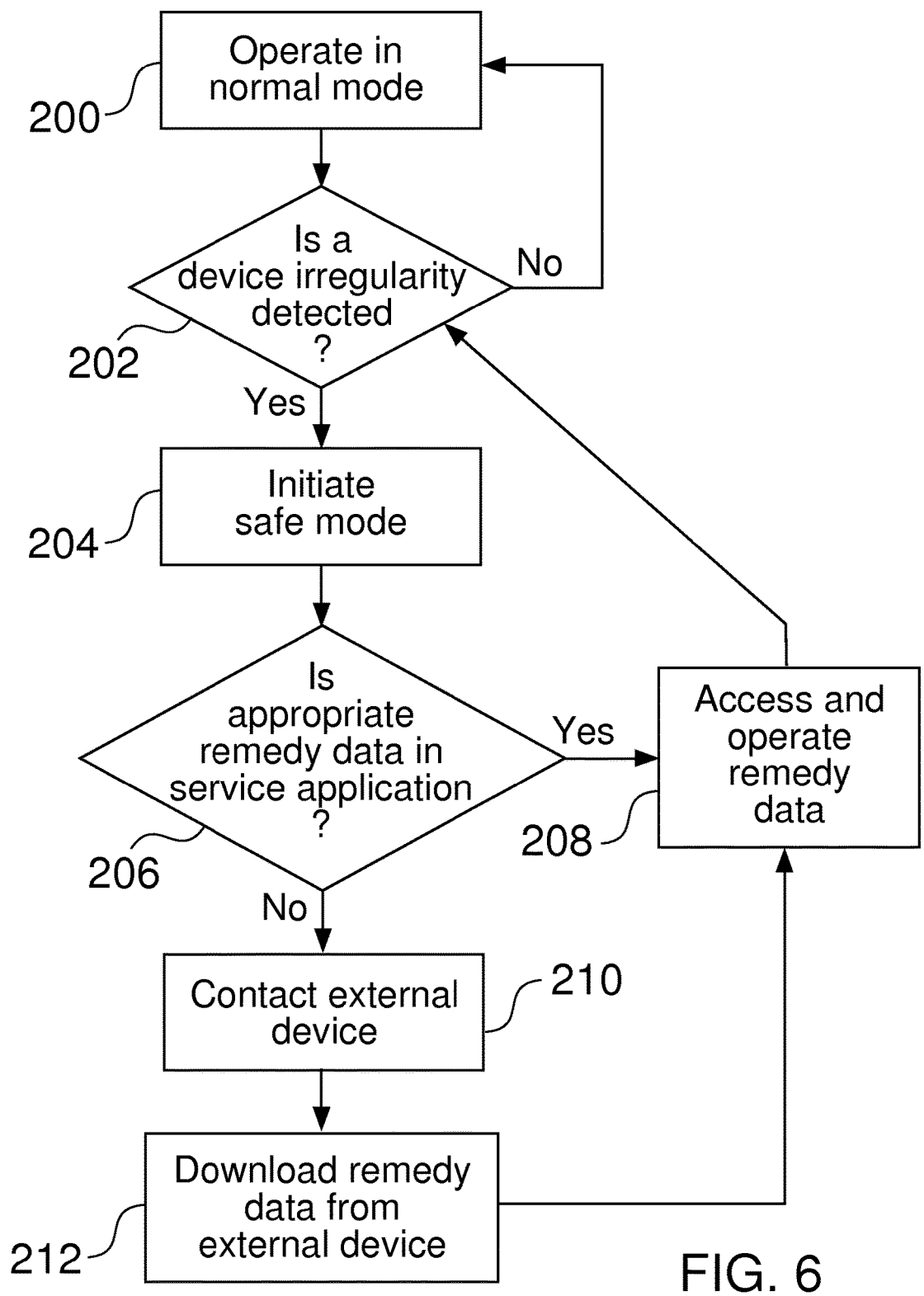
FIG. 6 illustrates a flow diagram of a method of operating an IMD, according to an embodiment of the present disclosure.

FIG. 6 illustrates a flow diagram of a method of operating an IMD, according to an embodiment of the present disclosure. At 200, the IMD is operated in a normal mode of operation. At 202, it is determined whether a device irregularity exists. For example, an interrogator of a firmware control module may monitor the IMD to determine whether any device irregularities are present. If no device irregularities exist, the process returns to 200.

If, however, a device irregularity exists, the process continues to 204, in which a base therapy mode is initiated. In the base therapy mode, a CPU of the firmware control module may access a subset of ROM, which may include a service application. At 206, the CPU searches the service application to determine whether appropriate remedy data exists for fixing the particular device irregularity. If the remedy data exists in the service application, the method proceeds 208, in which the CPU accesses and operates according to instructions within the remedy data to fix the device irregularity. The method then returns to 202.

If, however, the remedy data is not already in the service application, the CPU contacts the external device at 210 with the data regarding the device irregularity. The external device receives the device irregularity data and searches for appropriate remedy data. At 212, the external device sends the remedy data to the firmware control module, which downloads the remedy data. The method then proceeds to 208, in which the CPU accesses and operates according to instructions within the remedy the data in order to fix the device irregularity. The method then returns to 202.

Figure 7:
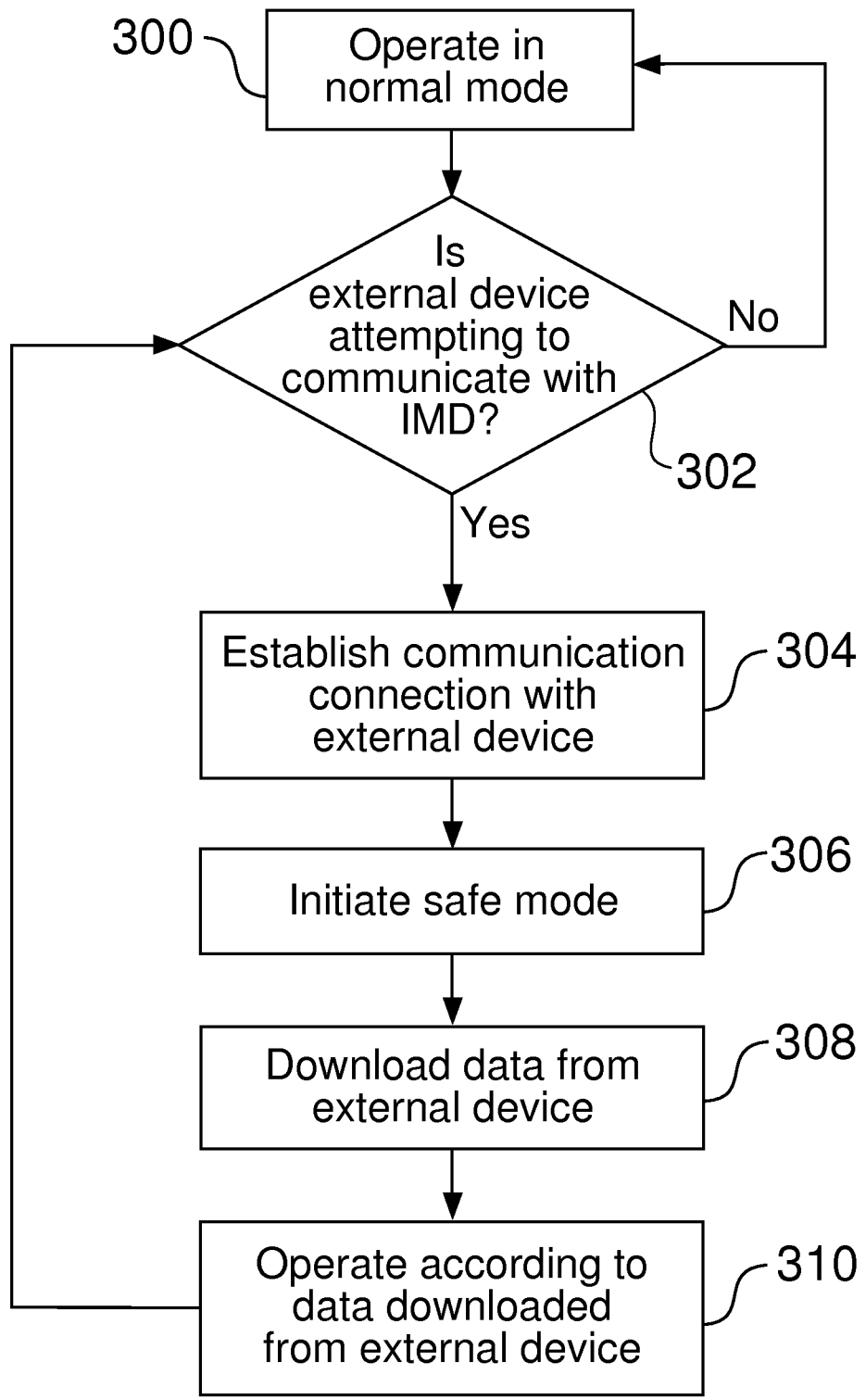
FIG. 7 illustrates a flow diagram of a method of operating an IMD, according to an embodiment of the present disclosure.

FIG. 7 illustrates a flow diagram of a method of operating an IMD, according to an embodiment of the present disclosure. At 300, the IMO operates in a normal mode. At 302, it is determined whether an external device is attempting to communicate with the IMD. For example, an interrogator or a firmware control module may monitor and sniff for communication signals from the external device. If the external device is not attempting to communicate with the IMO, the method returns to 300.

If, however, the external device is attempting to communicate with the IMD, the method proceeds to 304, in which a communication connection is established between the IMD and the external device. Next, at 306, the firmware control module initiates a base therapy mode. In the base therapy mode, data, such as device update data, may be downloaded to memory, such as RAM, ROM, EEPROM, and/or the like, from the external device at 308. At 310, the IMD operates according to the data downloaded from the external device. The method then returns to 302. Alternatively, the firmware control module may download update or updated data from the external device during a normal mode of operation.

Figure 8:
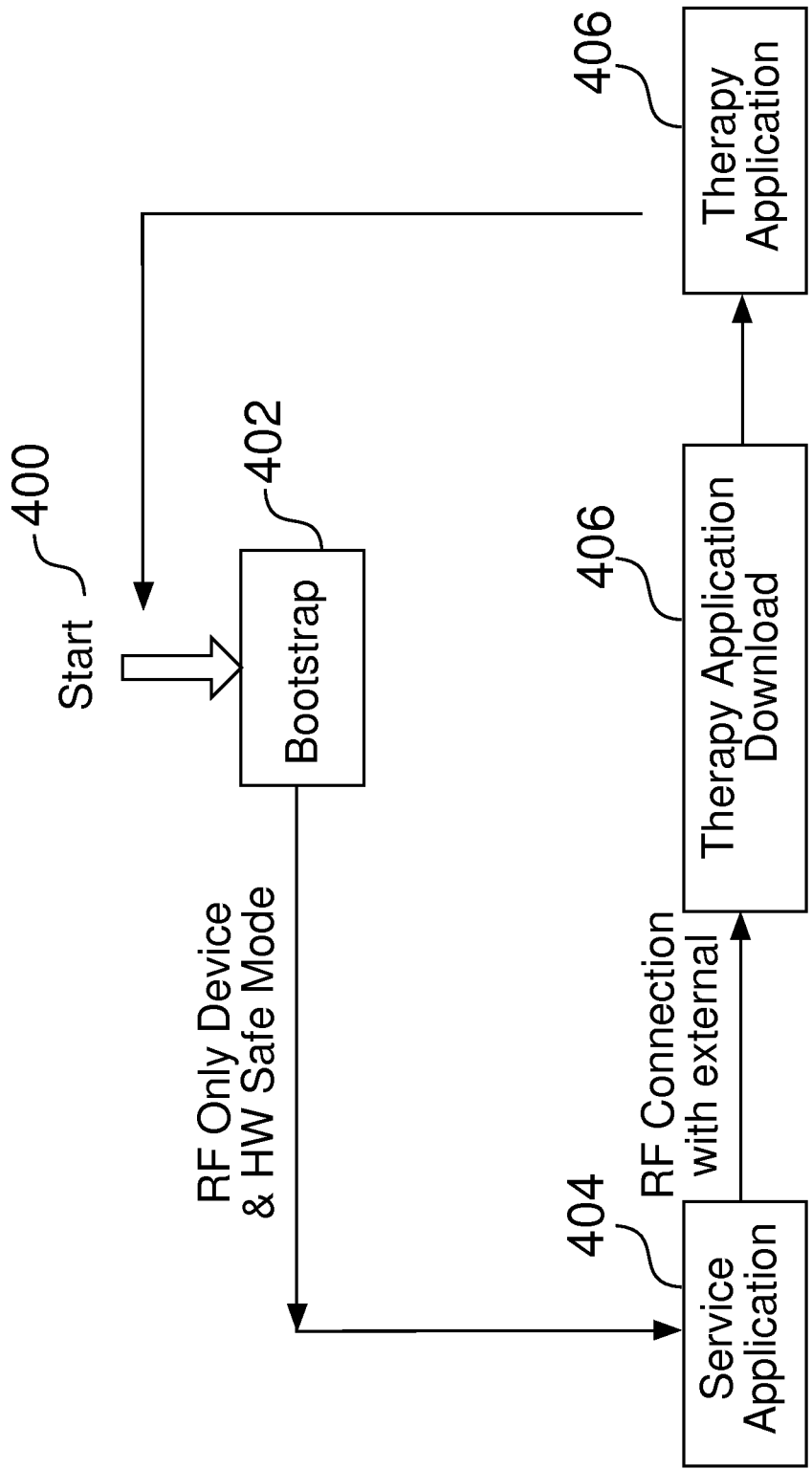
FIG. 8 illustrates a flow diagram of a method for implementing a service application operation, according to an embodiment of the present disclosure.

FIG. 8 illustrates a flow diagram of a method for implementing a service application operation, according to an embodiment of the present disclosure. FIG. 8 is a simplified illustration of an RF service application configured to support field updates/upgrades of the therapy application, such as may be included within the firmware control module (such as within RAM) and/or the therapy control module (such as within a therapy logic circuit). The method starts at 400, which may include an initial power-on, a controlled re-start for the purpose of a firmware upgrade or a normally-functioning IMD, or a re-start of the IMD after an error condition. The method then moves to 402, in which the IMD operates in a bootstrap mode (for example, the safe mode), in which the IMD operates independent of one or more hardware circuits of the IMD. Instead, the bootstrap 402 is configured to operate through just the service application, for example.

Next, at 404, the service application is initiated. As shown in FIG. 4, the service application may operate to download a therapy application at 406. The therapy application download may be a field upgrade of the IMD. For example, the field upgrade may provide the IMD with updated software and firmware while implanted within the patient (that is, not at a factory or distributor) that may provide increased and improved functionality to the IMD. At 406, once the field upgrade is complete, the service application 404 is deactivated and the therapy application is initiated. The therapy application may be a normal or standard mode of operation. In other words, the therapy application may represent operation of the IMD when it is not in the safe mode. The method then proceeds to detecting whether a start 400 event arises.

In short, when the service application downloads firmware, whether a device fix, update, or the like, the IMD performs basic therapeutic functions without the therapy application running. For example, the BTSM logic circuit 108, as shown in FIG. 4, operates when the service application download firmware.

Figure 9:
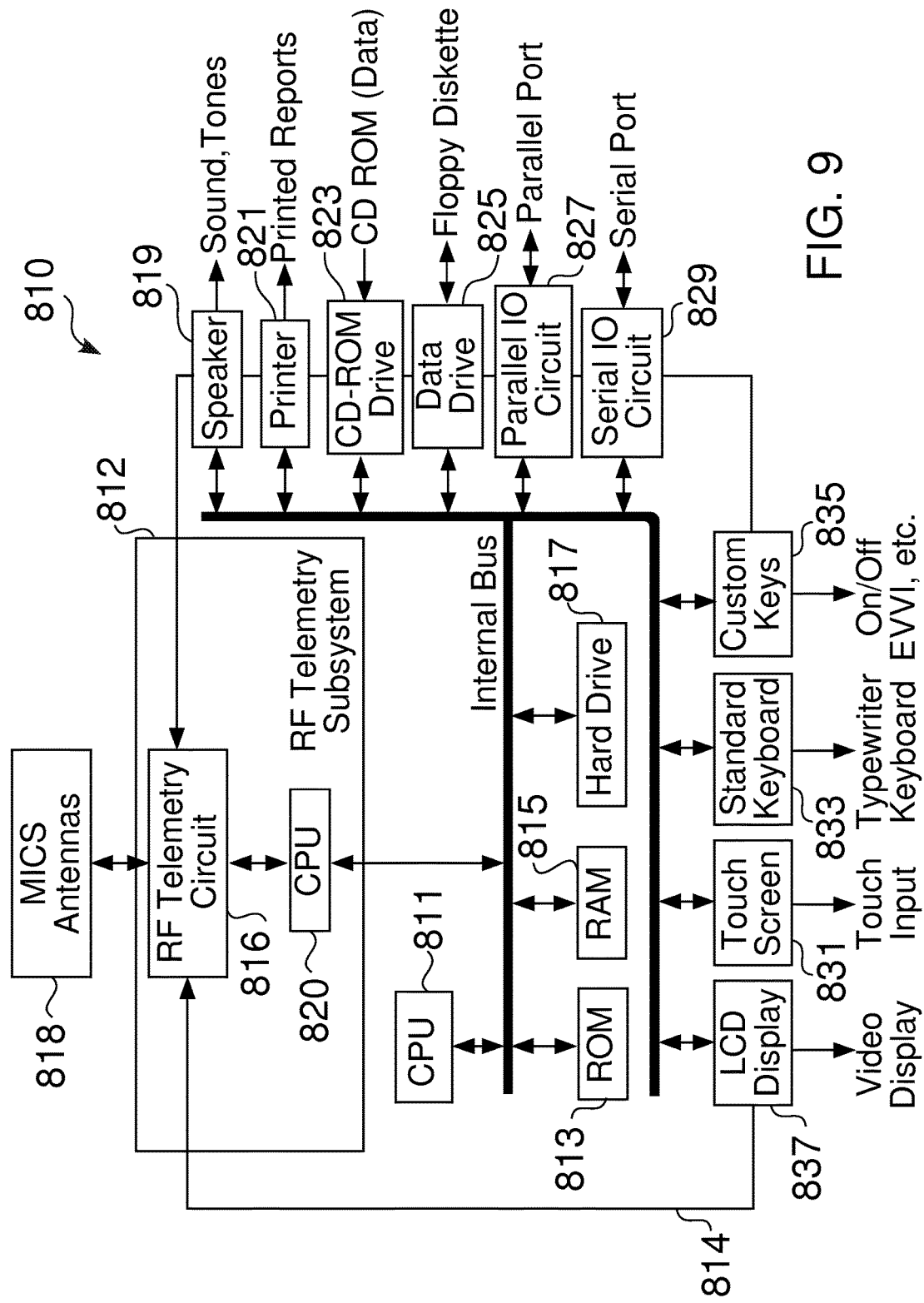
FIG. 9 illustrates a functional block diagram of an external device, according to an embodiment of the present disclosure.

FIG. 9 illustrates a functional block diagram of an external device 810, according to an embodiment of the present disclosure. The external device 810 may represent a handheld portable tablet-type programmer device used by physicians and others to communicate with, collect data from, program and reprogram, an IMD. Alternatively, the external device 810 may be a cell phone, personal computer, or laptop computer. Additionally, the external device 810 may be a standalone antenna assembly. Optionally, the external device 810 may be a patient care system, such as the Merlin® home patient care system offered by St. Jude Medical. The external device 810 may include an RF telemetry subsystem 812 that communicates with an implantable medical device (IMD) and/or a network 814. The telemetry subsystem 812 includes an RF telemetry circuit 816 operatively connected to one or more MICS antennas 818. The telemetry circuit 816 is also operatively connected to a controller or processing unit 820.

The external device 810 may be a workstation, a portable computer, an IMD programmer, a PDA, a cell phone and the like. The external device 810 may include an internal bus that connects/interfaces with a Central Processing Unit (CPU) 811, ROM 813, RAM 815, a hard drive 817, speaker 819, a printer 821, a CD-ROM drive 823, a data drive 825, a parallel I/O circuit 827, a serial I/O circuit 829, a display 837, a touch screen 831, a standard keyboard connection 833, custom keys 835, and the RF telemetry subsystem 812. The internal bus may include an address/data bus that transfers information between the various components described herein. The hard drive 817 may store operational programs as well as data, such as waveform templates and detection thresholds.

The CPU 811 may include a microprocessor, a microcontroller, or equivalent control circuitry, designed specifically to control interfacing with the external device 810 and with the IMD or network 814. The CPU 811 may include RAM or ROM memory, logic and timing circuitry, state machine circuitry, and I/O circuitry to interface with the IMD. The touch screen 831 may display graphic information relating to the IMD and/or the network 814. The touch screen 831 is configured to accept a user's touch input when selections are made. The keyboard 833 (for example, a "QWERTY" typewriter keyboard) is configured to allow a user to enter data into the displayed fields, as well as interface with the RF telemetry subsystem 812. Further, the custom keys 835 are configured to selectively turn on/off (for example, EVVI) the external device 810. The printer 821 is configured to print copies of reports for a physician to review or to be placed in a patient file, and the speaker 819 is configured to provide an audible warning (for example, sounds and tones) to the user. The parallel I/O circuit 827 interfaces with a parallel port. The serial I/O circuit 829 interfaces with a serial port. The data drive 825 is configured to accept data disks, for example. Optionally, the data drive 825 may be a USB port or other interface capable of communicating with a USB device such as a memory stick. The CD-ROM drive 923 accepts CD ROMs.

As noted above, the RF telemetry subsystem 812 may include the central processing unit (CPU) 820 in electrical communication with the RF telemetry circuit 816. The telemetry circuit 816 may be connected to implantable leads to receive and process cardiac signals. Optionally, the cardiac signals sensed by the leads may be collected by an IMD and then wirelessly transmitted to the telemetry subsystem 812 of the external device 810.

Figure 10:
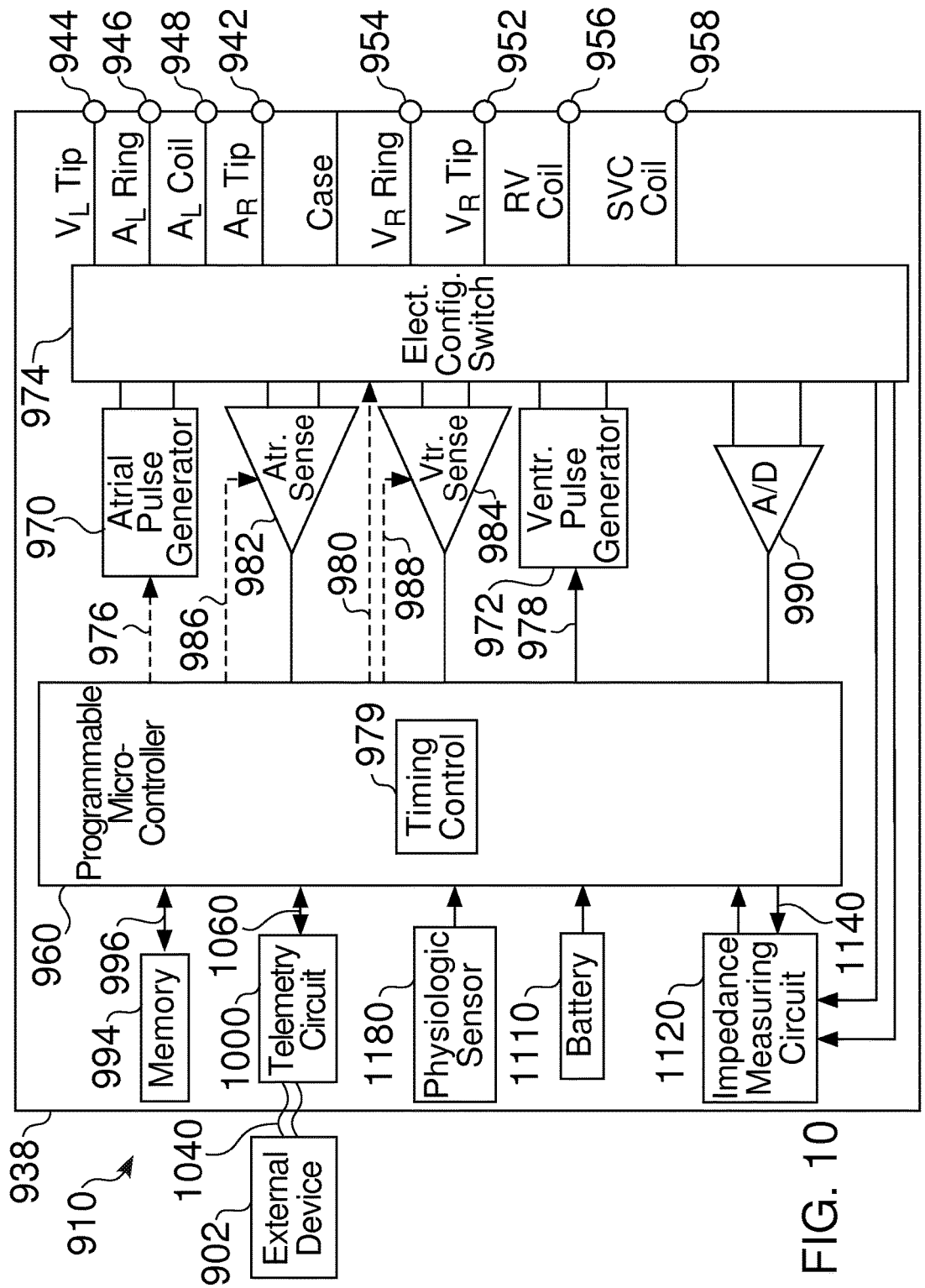
FIG. 10 illustrates a block diagram of exemplary internal components of an IMD, according to an embodiment of the present disclosure.

FIG. 10 illustrates a block diagram of exemplary internal components of an IMD 910, according to an embodiment of the present disclosure. It is to be noted that the IMD 910 is but one example of an IMD that may be used with embodiments of the present disclosure. Various other IMDs may be used in place of the IMD 910. The IMD 910 is for illustration purposes only, and it is understood that the circuitry could be duplicated, eliminated or disabled in any desired combination to provide a device capable of treating patient anatomy with cardioversion, defibrillation and/or pacing stimulation as well as providing for apnea detection and therapy. The IMD 910 includes a housing 938, which is shown schematically in FIG. 10. The housing 938 is often referred to as the "can", "case" or "case electrode" and may be programmably selected to act as the return electrode for all "unipolar" modes. The housing 938 may further be used as a return electrode alone or in combination with one or more of the coil electrodes for shocking purposes. The housing 938 further includes a connector (not shown) having a plurality of terminals, 942, 952, 954, 956 and 958 (shown schematically and, for convenience, the names of the electrodes to which they are connected are shown next to the terminals). A right atrial tip terminal ($A_R$ TIP) 942 is adapted for connection to an atrial tip electrode and a right atrial ring terminal may be adapted for connection to a right atrial ring electrode. A left ventricular tip terminal ($V_L$ TIP) 944, a left atrial ring terminal ($A_L$ RING) 946, and a left atrial shocking terminal ($A_L$ COIL) 948 are adapted for connection to a left ventricular ring electrode, a left atrial tip electrode, and a left atrial coil electrode, respectively. A right ventricular tip terminal ($V_R$ TIP) 952, a right ventricular ring terminal ($V_R$ RING) 954, a right ventricular shocking terminal ($R_V$ COIL) 956, and an SVC shocking terminal (SVC COIL) 958 are adapted for connection to a right ventricular tip electrode, right ventricular ring electrode, an RV coil electrode, and an SVC coil electrode, respectively.

The IMD 910 includes a programmable microcontroller 960 which controls operation. The microcontroller 960 (also referred to herein as a processor module or unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 960 includes the ability to process or monitor input signals (data) as controlled by program code stored in memory. The details of the design and operation of the microcontroller 960 are not critical to the invention. Rather, any suitable microcontroller 960 may be used that carries out the functions described herein. Among other things, the microcontroller 960 receives, processes, and manages storage of digitized cardiac data sets from the various sensors and electrodes. For example, the cardiac data sets may include pressure data, heart sound data, and the like.

The IMD 910 includes an atrial pulse generator 970 and a ventricular/impedance pulse generator 972 to generate pacing stimulation pulses for delivery by the right atrial lead, the right ventricular lead, and/or the coronary sinus lead via an electrode configuration switch 974. It is understood that in order to provide stimulation therapy in each of the four chambers of the heart, the atrial and ventricular pulse generators, 970 and 972, may include dedicated, independent pulse generators, multiplexed pulse generators or shared pulse generators. The pulse generators, 970 and 972, are controlled by the microcontroller 960 via appropriate control signals, 976 and 978, respectively, to trigger or inhibit the stimulation pulses.

The microcontroller 960 further includes timing control circuitry 979 used to control the timing of such stimulation pulses (e.g., pacing rate, atria-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, and the like. Switch 974 includes a plurality of switches for connecting the desired electrodes to the appropriate I/O circuits, thereby providing complete electrode programmability. Accordingly, the switch 974, in response to a control signal 980 from the microcontroller 960, determines the polarity of the stimulation pulses (e.g., unipolar, bipolar, etc.) by selectively closing the appropriate combination of switches (not shown) as is known in the art.

Atrial sensing circuit 982 and ventricular sensing circuit 984 may also be selectively coupled to the right atrial lead, coronary sinus lead, and the right ventricular lead, through the switch 974 for detecting the presence of cardiac activity in each of the four chambers of the heart. Accordingly, the atrial (ATR SENSE) and ventricular (VTR SENSE) sensing circuits, 982 and 984, may include dedicated sense amplifiers, multiplexed amplifiers or shared amplifiers. The outputs of the atrial and ventricular sensing circuits, 982 and 984, are connected to the microcontroller 960 which, in turn, are able to trigger or inhibit the atrial and ventricular pulse generators, 970 and 972, respectively, in a demand fashion in response to the absence or presence of cardiac activity in the appropriate chambers of the heart.

Cardiac signals are also applied to the inputs of an analog-to-digital (A/D) data acquisition system 990. The data acquisition system 990 is configured to acquire signals, convert the raw analog data into a digital signal, and store the digital IEGM signals in memory 994 for later processing and/or telemetric transmission to an external device 902. The data acquisition system 990 is coupled to the right atrial lead, the coronary sinus lead, and the right ventricular lead through the switch 974 to sample cardiac signals across any combination of desired electrodes.

The microcontroller 960 may include a firmware control module, such as described above. The microcontroller 960 is coupled to memory 994 by a suitable data/address bus 996, wherein the programmable operating parameters used by the microcontroller 960 are stored and modified, as required, in order to customize the operation of IMO 910 to suit the needs of a particular patient. The memory 994 also stores data sets (raw data, summary data, histograms, etc.), such as the IEGM data, heart sound data, pressure data, SvO2 data and the like for a desired period of time (e.g., 1 hour, 24 hours, 1 month, etc.). The memory 994 may store instructions to direct the microcontroller 960 to analyze the cardiac signals and heart sounds, identify characteristics of interest, and derive values for predetermined statistical parameters. The IEGM, pressure, and heart sound data stored in memory 994 may be selectively stored at certain time intervals, such as 5 minutes to 1 hour periodically or surrounding a particular type of arrhythmia of other irregularity in the heart cycle. For example, the memory 994 may store data for multiple non-consecutive 10 minute intervals.

The pacing and other operating parameters of the IMD 910 may be non-invasively programmed into the memory 994 through a telemetry circuit 1000 in telemetric communication with the external device 902, such as a programmer, trans-telephonic transceiver or a diagnostic system analyzer, or with a bedside monitor. The telemetry circuit 1000 is activated by the microcontroller 960 by a control signal 1060. The telemetry circuit 1000 allows intra-cardiac electrograms, pressure data, acoustic data, SvO2 data, status information, and the like, as described above relating to the operation of IMD 910 (as contained in the microcontroller 960 or memory 994) to be sent to the external device 902 through an established communication link 1040.

The IMD 910 may also include an accelerometer or other physiologic sensor 1080, commonly referred to as a "rate-responsive" sensor because it is typically used to adjust pacing stimulation rate according to the exercise state of the patient. Optionally, the physiological sensor 1080 may further be used to detect changes in cardiac output, changes in the physiological condition of the heart, or changes in activity (e.g., detecting sleep and wake states) and to detect arousal from sleep. While shown as being included within IMD 910, it is to be understood that the physiologic sensor 1080 may also be external to IMD 910, yet still be implanted within or carried by the patient. A common type of rate responsive sensor is an activity sensor incorporating an accelerometer or a piezoelectric crystal, which is mounted within the housing 938 of IMD 910. The physiologic sensor 1080 may be used in conjunction with, or in place of, the position detector 965, for example.

The IMD 910 also includes a battery 1100, which provides operating power to all of the circuits shown. The IMD 910 is shown as having impedance measuring circuit 1120 which is enabled by the microcontroller 960 via a control signal 1140. Herein, impedance is primarily detected for use in evaluating ventricular end diastolic volume (EDV) but is also used to track respiration cycles. Other uses for an impedance measuring circuit include, but are not limited to, lead impedance, surveillance during the acute and chronic phases for proper lead positioning or dislodgement, detecting operable electrodes and automatically switching to an operable pair if dislodgement occurs, measuring respiration or minute ventilation; measuring thoracic impedance for determining shock thresholds; detecting when the device has been implanted, measuring stroke volume, and detecting the opening of heart valves, etc. The impedance measuring circuit 1120 is advantageously coupled to the switch 974 so that impedance at any desired electrode may be obtained.

Embodiments of the present disclosure provide an IMD that is able to communicate with an external device without the use of inductive communication. Instead, embodiments disclose an IMD that may include a firmware control module that is configured to switch to a base therapy mode during communication with, and through the command of, an external device, for example. During the base therapy mode, a therapy control module operates to provide basic, life-critical functionality to a patient, while a control unit of the firmware control module accesses a service application that may be a subset of memory, such as a segment of ROM. The service application may be accessed in order to remedy device irregularities, or to download system updates, for example.

Various embodiments described herein provide a tangible and non-transitory (for example, not an electric signal) machine-readable medium or media having instructions recorded thereon for a processor or computer to operate a system to perform one or more embodiments of methods described herein. The medium or media may be any type of CD-ROM, DVD, floppy disk, hard disk, optical disk, flash RAM drive, or other type of computer-readable medium or a combination thereof.

The various embodiments and/or components, for example, the control units, modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor may also include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer" or "module."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" may be interchangeable, and include any computer program stored in memory for execution by a computer, including RAM memory, ROM memory, EEPROM memory, and non-volatile RAM (NVRAM) memory. The above memory types are exemplary only, and are thus not limiting as to the types of memory usable for storage of a computer program.

While various spatial and directional terms, such as top, bottom, lower, mid, lateral, horizontal, vertical, front, and the like may be used to describe embodiments, it is understood that such terms are merely used with respect to the orientations shown in the drawings. The orientations may be inverted, rotated, or otherwise changed, such that an upper portion is a lower portion, and vice versa, horizontal becomes vertical, and the like.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112, sixth paragraph, unless and until such claim limitations expressly use the phrase "means for" followed by a statement of function void of further structure.

What is claimed is:

1. An implantable medical device (IMD) configured to be implanted within a patient and communicate with an external device remote from the patient, the IMD comprising:
   a communication module configured to wirelessly communicate over an RF link with the external device;
   a therapy control module configured to deliver therapy to the patient, the therapy control module including a reprogrammable therapy microprocessor configured to operate the therapy control module in a reprogrammable mode of operation, and a base-therapy state machine (BTSM) logic circuit separate from the reprogrammable therapy microprocessor, the BTSM logic circuit configured to transition between a finite number of states to operate the therapy control module in a base therapy mode of operation;
   a firmware control module including a central processing unit (CPU) and a memory; and
   a service application stored in the memory, the firmware control module configured to launch the service application and to switch operation from the reprogrammable therapy microprocessor to the BTSM logic circuit such that the BTSM logic circuit provides a base level of sensing and pacing therapy while the communications module in parallel maintains the RF link with the external device.

2. The IMD of claim 1, wherein the firmware control module launches the service application upon detection of one or both of a device irregularity or a communication signal from the external device, wherein the service application is configured to one or both of remedy the device irregularity or update the IMD.

3. The IMD of claim 2, wherein the firmware control module further includes an interrogator configured to monitor operation of the IMD and detect the one or both of the device irregularity or the communication signal from the external device.

4. The IMD of claim 2, wherein the device irregularity includes one or more of attempts by the CPU to write to a restricted portion of the memory, corruption of a portion of the memory, the therapy control module administering improper therapy to a patient, or overly-attenuated signal transmission.

5. The IMD of claim 2, wherein the communication signal from the external device includes update data configured to update firmware or software of at least a portion of the IMD.

6. The IMD of claim 1, wherein the firmware control module is configured to initiate an uncontrolled launch of the service application when one or more of the communication module, the therapy control module, or the firmware control module are malfunctioning, and wherein the firmware control module receives an error signal when one or more of the communication module, the therapy control module, or the firmware control module are malfunctioning that triggers the uncontrolled launch of the service application.

7. The IMD of claim 1, wherein the service application is configured to support RF-based firmware download and allow the launch of a clinical firmware application.

8. The IMD of claim 1, wherein the reprogrammable therapy microprocessor is deactivated when the service application is launched.

9. The IMD of claim 1, wherein the service application is configured to record an instantaneous functional operational state of one or more of the communication module, the firmware control module, and therapy control module when the service application is activated.

10. The IMD of claim 1, wherein the firmware control module further comprises a scratchpad memory, and wherein the CPU is configured to access the scratchpad memory during the base therapy mode.

11. The IMD of claim 1, further comprising a patient connection interface operatively connected to the therapy control module, wherein the patient connection interface is configured to connect the therapy control module to at least one anatomical structure of the patient.

12. The IMD of claim 1, wherein the BTSM logic circuit provides the base level of sensing and pacing therapy while at a same time the communications module in parallel transmits and/or receives RF signals to and/or from the external device.

13. The IMD of claim 1, wherein the firmware control module further comprises a random access memory (RAM), and wherein the CPU is prevented from accessing the RAM during the base therapy mode.

14. The IMD of claim 1, wherein the communication module comprises one or more of an RF transceiver and an RF antenna, wherein the communication module is configured to communicate with the external device through RF signals.

15. The IMD of claim 1, further comprising a switch connected to the reprogrammable therapy microprocessor and the BTSM logic circuit, the switch to deactivate the reprogrammable therapy microprocessor in connection with switching operation to the BTSM logic circuit.

16. The IMD of claim 1, wherein the memory of the firmware control module includes read-only memory (ROM), and wherein the ROM includes the service application.

17. A method of operating an implantable medical device (IMD) that is implanted within a patient, the method comprising:
    wirelessly communicating with an external device over an RF link using a communication module of the IMD;
    delivering therapy to a patient with a therapy control module, wherein the delivering operation includes operating the therapy control module in a reprogrammable mode of operation using a reprogrammable therapy microprocessor configured to operate the therapy control module in a reprogrammable mode of operation, and operating the therapy control module in a base therapy mode of operation using a base-therapy state machine (BTSM) logic circuit that is separate from the reprogrammable therapy microprocessor, the BTSM logic circuit transitions between a finite number of states; and
    launching a service application with a firmware control module; and
    deactivating the reprogrammable therapy logic circuit and switching operation to the BTSM logic circuit such that the BTSM logic circuit provides a base level of sensing and pacing therapy while the communications module maintains the RF link with the external device.

18. The method of claim 17, wherein the launching operation is initiated upon detection of one or both of a device irregularity or a communication signal from the external device, and wherein the launching operation includes remedying the device irregularity or updating the IMD.

19. The method of claim 18, further comprising monitoring operation of the IMD with an interrogator and detecting the one or both of the device irregularity or the communication signal from the external device.

20. The method of 17, wherein the launching operation further comprises:

receiving an error signal at the firmware control module, wherein the error signal related to a malfunction of one or more of the firmware control module, the therapy control module, or the communication module; and initiating an uncontrolled launch of the service application upon receipt of the error signal.

21. The method of claim 17, wherein the service application is configured to support RF-based firmware download and allow the launch of a clinical firmware application.

22. The method of claim 17, wherein the launching operation comprises deactivating the reprogrammable therapy microprocessor.

23. The method of claim 17, further comprising recording an instantaneous functional operational state of one or more of the communication module, the firmware control module, and therapy control module when the service application is activated.

24. The method of claim 17, further comprising accessing a scratchpad memory during the base therapy mode.

* * * * *